US008961883B2

(12) United States Patent
Song et al.

(10) Patent No.: US 8,961,883 B2
(45) Date of Patent: Feb. 24, 2015

(54) BIOCHIP INCLUDING CONDUCTIVE PARTICLE AND DEVICE FOR DETECTING TARGET ANTIGEN COMPRISING THE SAME

(75) Inventors: Kyuho Song, Seoul (KR); Sunkil Kang, Seoul (KR); Dayeon Kang, Seoul (KR); Taeyoung Kim, Seoul (KR); Seungmok Han, Seoul (KR); Gueisam Lim, Seoul (KR); Jisu Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 13/981,964

(22) PCT Filed: Feb. 7, 2012

(86) PCT No.: PCT/KR2012/000858
§ 371 (c)(1),
(2), (4) Date: Jul. 26, 2013

(87) PCT Pub. No.: WO2012/108651
PCT Pub. Date: Aug. 16, 2012

(65) Prior Publication Data
US 2013/0323827 A1    Dec. 5, 2013

(30) Foreign Application Priority Data
Feb. 10, 2011 (KR) .................. 10-2011-0011943

(51) Int. Cl.
*G01N 15/06* (2006.01)
*G01N 33/00* (2006.01)
*G01N 33/48* (2006.01)

(52) U.S. Cl.
USPC .......... 422/129; 422/502; 422/503; 422/68.1; 422/82.01; 422/82.02; 436/43; 436/149

(58) Field of Classification Search
CPC ........ G01N 15/06; G01N 33/00; G01N 33/48
USPC .............. 422/68.1, 82.01, 82.02; 436/43, 149
See application file for complete search history.

(56) References Cited

U.S. PATENT DOCUMENTS

2010/0009432 A1    1/2010  Lee et al.

FOREIGN PATENT DOCUMENTS

JP    2010-175327 A    8/2010
KP    10-0869909 B1    11/2008

OTHER PUBLICATIONS

Chang et al., "Effect of Different Gold Nanoparticle Sizes to Build an Electrical Detection DNA between Nanogap Electrodes," ScienceDirect, Microelectronic Engineering, No. 84, Feb. 15, 2007, 4 pages.

*Primary Examiner* — Brian J Sines
(74) *Attorney, Agent, or Firm* — Birch, Stewart, Kolasch & Birch, LLP

(57) ABSTRACT

A biochip including conductive particle and a device for detecting target antigen comprising the biochip are disclosed. According to the present invention, a target antigen can be effectively detected using a small amount of target antigen alone, whereby nonspecific detection signal can be reduced and an amplified signal can be detected.

7 Claims, 2 Drawing Sheets

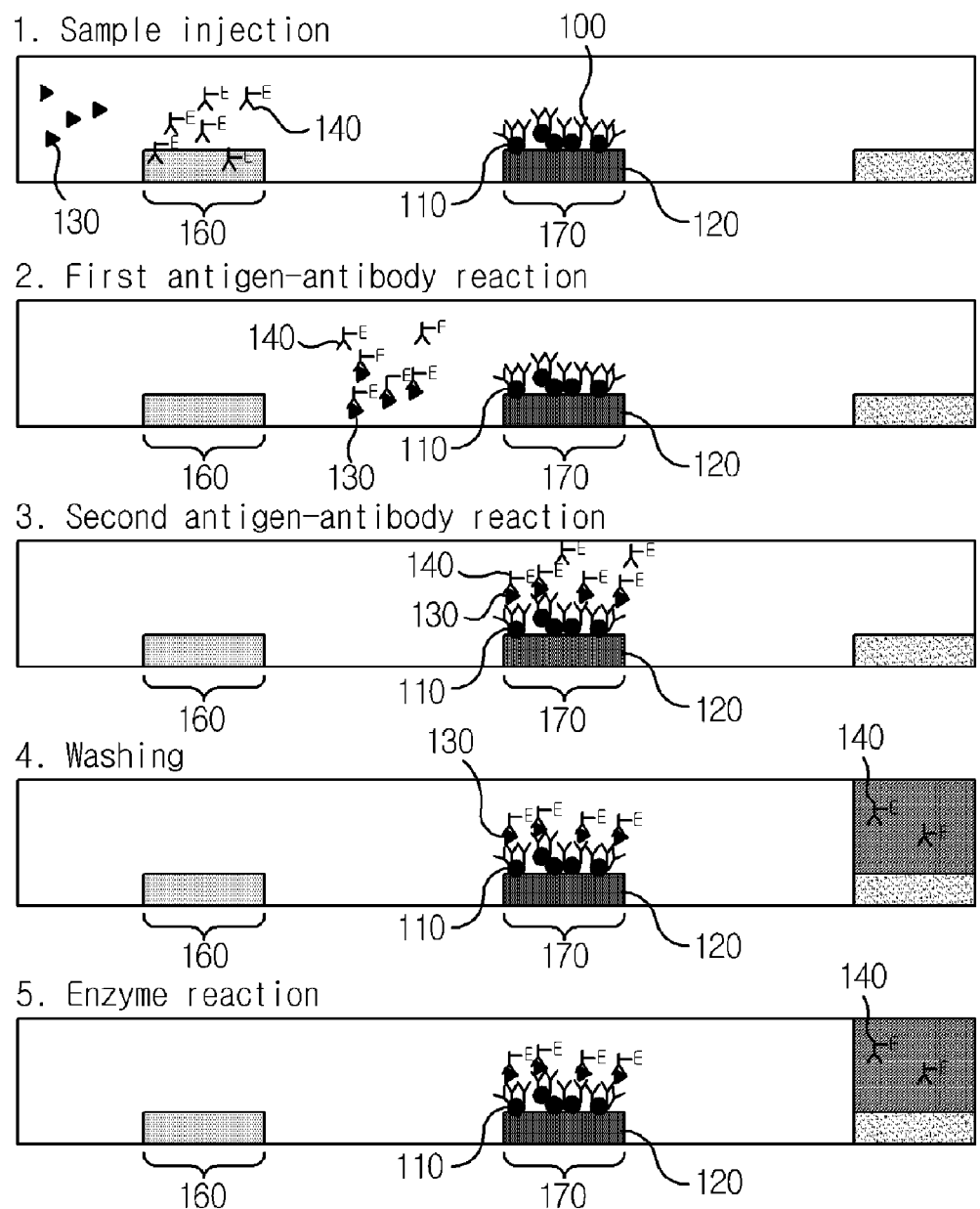

BIOCHIP INCLUDING CONDUCTIVE PARTICLE AND DEVICE FOR DETECTING TARGET ANTIGEN COMPRISING THE SAME

TECHNICAL FIELD

The teachings in accordance with the exemplary embodiments of this present invention generally relate to a biochip including conductive particle and a device for detecting target antigen comprising the same.

BACKGROUND ART

A point-of-care test is a rapid test examination to obtain information related to diseases by using body fluids of a general person. A variety of structural approaches related to formation of a detector has been waged as an attempt to obtain a lower detection threshold (high detection performance).

Particularly, attempts have been waged to increase the surface area to volume (SA/V) ratio by forming a 3-D detector using polymer matrix, polystyrene nano particle, silica nano particle or magnetic nano particle. These attempts are intended to detect a high signal by increasing antigen-antibody reaction through increase SA/V ratio of the detector.

However, application of the 3-D structure to electrochemical assay suffers from disadvantages in that specimen or electrons generated from the specimen that flow to an electrode surface deteriorates a diffusing speed due to structural deformation, whereby a finally measured signal rather shows an attenuated form.

A conventional detector using the polymer matrix is such that antigen binds to an antibody having an enzyme, an injected analyte is oxidized to generate electrons, and the generated electrons flows into a metal electrode along a path through the polymer matrix. A final current value is measured by an amount of flown current. However, a diffusing speed of electron is restricted by types and thickness of the polymer matrix. Furthermore, the formed polymer matrix itself acts a resistance to generate an IR degradation phenomenon, whereby more voltage than is necessary is disadvantageously required to generate a power loss.

Meantime, a biochip is a typical example in which new nanotechnology (NT), biotechnology (BT), and information technology (IT) are converged. The biochip is a technology in which a material technology such as NT, BT, which is an application field and contents of the technology, and IT technology that analyzes a result or a large amount of results are converged.

The biochip is formed by high-density micro-arraying various kinds of detection materials, for example, a biomaterial at a surface of a solid-phase support body of a unit area, and is classified into various kinds of chips such as a DNA chip, a protein chip, a cell chip, and a neuron chip according to a biomaterial for attaching to a surface thereof. Further, the biochip has been developed into a lab-on-a-chip (LOC) by converging with micro-fluidic technology.

A research for improving accuracy of an inspection and storability of the biochip through the biochip has been performed. Further, a research for increasing a reaction ratio of the biochip has been performed.

DISCLOSURE OF INVENTION

Technical Problem

The present invention has been made to solve the disadvantages of the prior art and therefore an object of certain embodiments of the present invention is to provide a biochip including conductive particle connected with polymer material, provided on a surface of a metal electrode substrate.

Another object of certain embodiments of the present invention is to provide a device for detecting target antigen comprising a biochip.

Technical subjects to be solved by the present invention are not restricted to the above-mentioned description, and any other technical problems not mentioned so far will be clearly appreciated from the following description by the skilled in the art. That is, the present invention will be understood more easily and other objects, characteristics, details and advantages thereof will become more apparent in the course of the following explanatory description, which is given, without intending to imply any limitation of the disclosure, with reference to the attached drawings.

Solution to Problem

An object of the invention is to solve at least one or more of the above problems and/or disadvantages in whole or in part and to provide at least advantages described hereinafter. In order to achieve at least the above objects, in whole or in part, and in accordance with the purposes of the invention, as embodied and broadly described, and in one general aspect of the present invention, there is provided a biochip, the biochip characterized by: a substrate, the substrate having an electrode surface, the electrode surface coupled to conductive particle, the conductive particle coupled to polymer material; and a current detector connected to the substrate.

The present invention relates to a biochip for point-of-care test, and particularly to a biochip configured to effectively obtain an electrical signal detectable by analyte.

The polymer material may be any material that wants to be analyzed, and may be comprised of one or more selected from a group consisting of antibody, antigen, nucleic acid, carbohydrate and cell. The polymer material may be preferably antibody. The polymer material may be connected to conductive particle.

A method for connecting the polymer material to the conductive particle is not particularly limited. For example, a surface of a substrate may be initially arranged with a conductive particle, and a polymer material may be connected to the conductive particle thus arranged. Alternatively, the polymer material and the conductive particle are connected in the first place, and then, the connector thus connected may be arranged on the surface of the substrate.

The conductive particle is used as a medium for transmitting electrons to the metallic electrode substrate. The conductive particle may be comprised of one or more selected from a group consisting of compound semiconductor, metal oxide semiconductor, silicone semiconductor, fullerene derivative, carbon nanotube derivative, graphene derivative, pentacene derivative and thiophene derivative. However, the conductive particle is not limited thereto. The conductive particle may be preferably titanium oxide nano particle.

In some exemplary embodiments, but not necessarily, the conductive particle connected with the polymer material may be arranged on a surface of an electrode of a substrate. Furthermore, the substrate is connected to a current detector to rapidly and accurately detect a flow of current transmitted to the substrate in terms of amount of current. To this end, the conductive particle may be preferably and concentratively arranged on a surface of an electrode, may be preferably stacked in two or more layers, and may take a 3-D shape on the surface of the electrode.

Material of substrate is not particularly limited, may be a metal substrate, and may be a substrate arranged on a surface with an electrode comprised of a metal. The metal usable for the substrate and/or for the electrode may be comprised of one or more selected from a group consisting of Ag, Pt, Au, copper, carbon and ITO (Indium Tin Oxide). However, the metal is not particularly limited.

In another general aspect of the present disclosure, there is provided a device for detecting target antigen, the device characterized by: a reactor including a substrate, the surface of which a first antibody is secured, the first antibody binding to detectable label and specifically binding to a target antigen; a substrate fluidly connected to the reactor and arranged on an electrode surface with a conductive particle connected to a second antibody specifically bound to the target antigen; and a current detector connected to the substrate.

In some exemplary embodiments, but not necessarily, the device for detecting target antigen comprising a biochip may include a reactor including a substrate, the surface of which a first antibody is secured, the first antibody binding to detectable label and specifically binding to a target antigen. Furthermore, the device according to the present invention may include the biochip according to the exemplary embodiment of the present invention.

Particularly, the polymer material may include a second antibody (detectable antibody) specifically bound to the antigen.

The detectable label means an atom or a molecule configured to specifically detect a molecule including a label among identical types of molecules having no label, where the detectable label may include colored bead, antigen binder, enzyme, chromophore material, fluorescent material, phosphor material, electrically detectable molecule, molecule or quantum dot providing changed fluorescent-polarization or changed light spread. However, the detectable label is not limited thereto.

Furthermore, the label may be radio isotopes such as $P^{32}$ and $S^{35}$, chemiluminescent compound, labeled bound protein, spectroscopic markers such as heavy metal atoms and dyes, and magnetic marker dyes. The dyes may include quinoline dye, triarylmethane dye, phthalein, azo dye and cyanine dye, for example. However, the label is not limited thereto.

The term of "nanoparticle" is a "particle having one or more dimensions of the order of 1000 nm or less", and preferably, a particle having a diameter in the range of 10 nm to 1000 nm. The ingredients comprising the nanoparticle may include metals such as Ag, Au, copper, aluminum, nickel, palladium and platinum, semiconductor materials such as DdSe, DdS, InAs and InP, an inactive substances such as polymeric materials including polystyrene, latex, acrylate and polypeptide, and may be comprised of one or more selected therefrom. However, the ingredients are not limited thereto.

The nanoparticle may bind to one or more detectable labels, and the number of bindable detectable labels may be determined by the size of the nanoparticle.

The method according to the present invention may be used for an immunosorbent assay method used for detection of a target antigen, particularly in capture-ELISA (enzyme-linked immunosorbent assay, enzyme-linked immunospecific assay).

The capture-ELISA generally includes: (i) coating a capture-antibody on a surface of a solid substrate; (ii) reacting the capture-antibody and specimen (e.g., specimen including antibody that becomes a target); (iii) binding a resultant of the step (ii) to a detectable label generating a signal, and reacting specifically reacting detection antibody to the target antibody; and (iv) measuring a signal generated from the detectable label.

Particularly, a signal generated from the detectable label may be measured in terms of amount of current by a current detector in response to flow of current transmitted to a metal electrode substrate of the biochip according to the exemplary embodiment of the present invention, and conductive particle included in the biochip serves to provide a path having a low resistance for the flow of the electron. Examples of the metal and conductive particle usable for the device according to the present invention are as per the explanation given in the foregoing.

Advantageous Effects of Invention

The biochip including conductive particle and the device for detecting target antigen comprising the biochip according to the present invention have an advantageous effect in that the target antigen can be effectively detected.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF DRAWINGS

FIG. 2 is a schematic view illustrating a method for detecting a target antigen using a device for detecting target antigen comprising a biochip including a conductive particle according to an exemplary embodiment of the present invention.

BEST MODE FOR CARRYING OUT THE INVENTION

Figure 1:
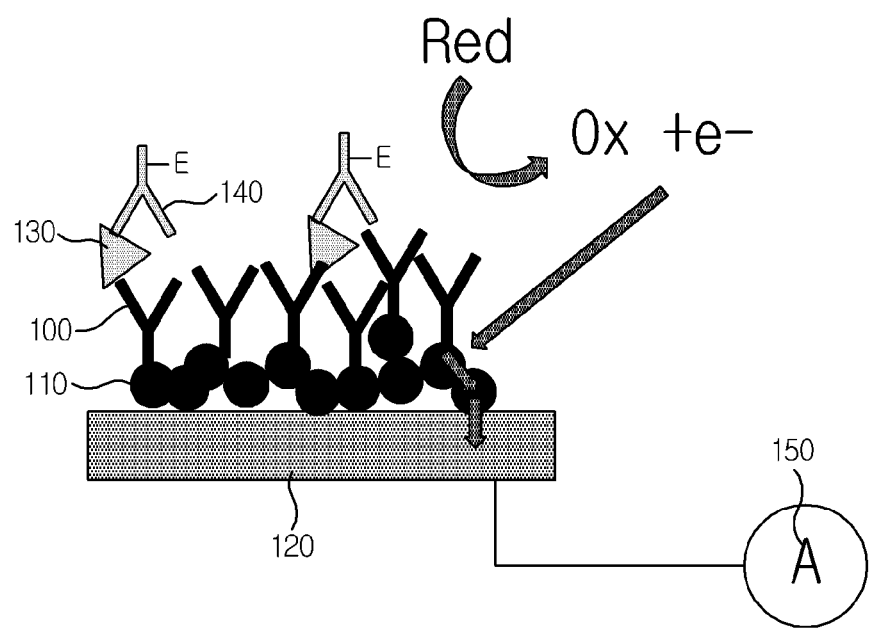
FIG. 1 is a mimetic diagram illustrating a biochip according to an exemplary embodiment of the present invention.

Before additional details are further described, it is to be understood that the subject matter described herein is not limited to the particular embodiments described, and as such may of course vary while keeping within the spirit and scope of the present invention. It is also to be understood that the terminology used herein is for the purpose of describing particular exemplary embodiments only, and is not intended to be limiting in any fashion, and in particular with respect to the doctrine of equivalents. Unless defined otherwise, all technical terms used herein have the same meaning as commonly understood by one skilled in the art to which this subject matter belongs.

That is, the present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

To more clearly and concisely describe and point out the subject matter of the claimed invention, the following definitions are provided for specific terms, which are used in the following description and the appended claims.

The term "antigen" is protein or peptide that evokes an immune response.

The term "antibody" is synonymous with "immunoglobulin," and includes naturally occurring human antibodies, polyclonal antibodies, and monoclonal antibodies. The term "antibody" is meant to include both the native antibody and biologically active and synthetic derivatives of antibodies, such as, for example, Fab', F(ab").sub.2 or Fv as well as single-domain and single-chain antibodies. A biologically active derivative of an antibody retains the ability to bind antigen.

Descriptions of well-known components and processing techniques are omitted so as to not unnecessarily obscure the embodiments of the disclosure.

Words such as "thereafter," "then," "next," "therefore", "thus", etc. are not intended to limit the order of the processes; these words are simply used to guide the reader through the description of the methods.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Thus, for example, reference to "a component" can include a combination of two or more components; reference to "fluid" can include mixtures of fluids, and the like.

It will be understood that, although the terms first, second, etc. may be used herein to describe various elements, these elements should not be limited by these terms. These terms are only used to distinguish one element from another. For example, a first region/layer could be termed a second region/layer, and, similarly, a second region/layer could be termed a first region/layer without departing from the teachings of the disclosure.

FIG. 1 is a mimetic diagram illustrating a biochip according to an exemplary embodiment of the present invention, and FIG. 2 is a schematic view illustrating a method for detecting a target antigen using a device for detecting target antigen comprising a biochip including a conductive particle according to an exemplary embodiment of the present invention.

Now, referring to FIGS. 1 and 2, the method for detecting a target antigen using the device for detecting target antigen comprising a biochip including a conductive particle according to an exemplary embodiment of the present invention will be explained.

FIG. 1 is a mimetic diagram illustrating a biochip according to an exemplary embodiment of the present invention, where a metal electrode substrate (120) arranged at a surface with a conductive particle (110) bound to a first antibody (100) is illustrated.

The first antibody (100) may be a capture antibody bindable to a target antigen. Furthermore, the metal electrode substrate (120) may be connected to a current detector (150) for measuring a current flowing in the substrate. The first antibody (100) may include different polymer materials, such as, for example, antibody, antigen, nucleic acid, carbohydrate and cell according to experimental purpose.

In some exemplary embodiments, the conductive particle (110) may be used as a carrier of electrons. The conductive particle (110) according to the present invention is a biochip configured to improve a diffusing speed and to amplify a finally-measured signal by providing a path having a low resistance in a process of electrons generated in a detection process of a target antigen being transmitted to the metal electron substrate (120), using an n-type semiconductor, for example.

Furthermore, formation of a biochip in 3-D structure may increase an SA/V (surface/volume) ratio, whereby reaction of a target antigen (130) and the first antibody (100) can be further increased. Particularly, a titanium oxide nanoparticle used as an n-type oxide semiconductor is known to have large electron mobility, and is advantageously easy to chemically bind to a carboxylated functional group of an antibody comprised of amino acid.

Referring to FIG. 1, electrons can be generated if injected biological specimen is oxidized, after a second antibody (140), in which the target antigen (130) and the detectable label (e.g., enzyme) are connected to the biochip through antigen-antibody reaction, is captured. The generated electrons move to the metal electron substrate (120) through a path according to n-type semiconductor, for example, and the current detector (150) can measure a final current value using amount of electrons moved to the metal electron substrate (120).

MODE FOR THE INVENTION

The method for detecting a target antigen using a device for detecting target antigen comprising a biochip including a conductive particle according to the exemplary embodiment of the present invention may be performed as per FIG. 2.

First of all, in a case a biological specimen including a detectable target antigen, for example, blood or body fluid, is injected into a device according to the present invention, a complex body is formed at the reactor (160) of the device through the antigen-antibody reaction of the target antigen (130) included in the specimen with the second antibody (140) pre-bound to the reactor (160).

Successively, the complex body experiences a second the antigen-antibody reaction at the detector (170) arranged at a surface with the conductive particle (110) bound to the first antibody (100) is 3-D structure. That is, the complex body is captured by the first antibody (100) on the conductive particle (110) arranged in three dimensionally on the surface of the metal electron substrate (120).

Thereafter, a not-captured remaining second antibody (140) is removed in a case a washing solution is injected into the metal electron sub substrate (120) on which the complex body is captured.

Then, the detector (170) induces an enzyme reaction by adding a substrate of enzyme connected to the second antibody (140). At this time, as shown in FIG. 1, the generated electrons are diffused and transmitted to the metal electron substrate, e.g., a gold electrode, through the conductive particle (110) having a high conductivity, e.g., an n-type semiconductor.

Now, the generated electrons can be measured as a current value by the current detector (150) connected to the metal electrode substrate (120).

The previous description of the present invention is provided to enable any person skilled in the art to make or use the invention. Various modifications to the invention will be readily apparent to those skilled in the art, and the generic principles defined herein may be applied to other variations without departing from the spirit or scope of the invention. Thus, the invention is not intended to limit the examples described herein, but is to be accorded the widest scope consistent with the principles and novel features disclosed herein.

INDUSTRIAL APPLICABILITY

As apparent from the foregoing, the biochip including conductive particle and the device for detecting target antigen comprising the biochip according to the present invention have an industrial applicability in that the target antigen can be effectively detected using a small amount of target antigen alone, whereby nonspecific detection signal can be reduced and an amplified signal can be detected.

The invention claimed is:

1. A device for detecting target antigen, the device comprising:
a reactor including a substrate, the surface of which a first antibody is secured, the first antibody binding to detectable label and specifically binding to a target antigen; a substrate fluidly but not directly connected to the reactor and arranged on an electrode surface with a conductive particle connected to a second antibody specifically bound to the target antigen; and
a current detector connected to the substrate.

2. The device of claim 1, wherein the conductive particle is comprised of one or more selected from the group consisting of a compound semiconductor, metal oxide semiconductor, silicone semiconductor, fullerene derivative, carbon nanotube derivative, graphene derivative, pentacene derivative and thiophene derivative.

3. The device of claim 1, wherein the conductive particle is titanium oxide nano particle.

4. The device of claim 1, wherein the conductive particle is concentratively arranged on a surface of an electrode.

5. The device of claim 1, wherein the conductive particle is stacked in two or more layers.

6. The device of claim 1, wherein the conductive particle takes a 3-D shape on the surface of the electrode.

7. The device of claim 1, wherein the electrode is comprised of one or more selected from the group consisting of Ag, Pt, Au, copper, carbon and ITO (Indium Tin Oxide).

* * * * *